United States Patent
Alferness et al.

(10) Patent No.: US 6,790,172 B2
(45) Date of Patent: *Sep. 14, 2004

(54) TISSUE RESECTION DEVICE, SYSTEM AND METHOD

(75) Inventors: Clifton A. Alferness, Redmond, WA (US); Hugo X. Gonzalez, Woodinville, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/287,188

(22) Filed: Nov. 4, 2002

(65) Prior Publication Data

US 2003/0083542 A1 May 1, 2003

Related U.S. Application Data

(63) Continuation of application No. 09/780,232, filed on Feb. 9, 2001, now Pat. No. 6,485,407, which is a continuation-in-part of application No. 09/534,244, filed on Mar. 23, 2000, now Pat. No. 6,328,689.

(51) Int. Cl.[7] ............................. A61F 2/00; A61H 19/00
(52) U.S. Cl. ............................................ 600/37; 601/153
(58) Field of Search ..................... 600/37, 16; 601/153; 452/116, 604, 227, 600, 606; 607/2, 129

(56) References Cited

U.S. PATENT DOCUMENTS

| | | |
|---|---|---|
| 5,167,568 A | 12/1992 | Esbroeck et al. |
| 5,558,617 A | 9/1996 | Heilman et al. |
| 5,702,343 A | 12/1997 | Alferness |
| 6,076,013 A | 6/2000 | Brennan et al. |
| 6,085,754 A | 7/2000 | Alferness et al. |
| 6,095,968 A | 8/2000 | Snyders |
| 6,123,663 A | 9/2000 | Rebuffat |
| 6,155,968 A | 12/2000 | Wilk |
| 6,328,689 B1 | 12/2001 | Gonzalez et al. |

*Primary Examiner*—Mary Beth Jones
*Assistant Examiner*—Nikita R Veniaminov
(74) *Attorney, Agent, or Firm*—Knobbe, Martens, Olson & Bear LLP

(57) ABSTRACT

A resection device and method permits safe and efficient encapsulation, isolation and resection of body tissue. The device includes a sheath of flexible and severable material configured to receive the body tissue to be resectioned as it is drawn therein. The sheath may be expandable and held in an expanded condition as the body tissue to be resectioned is drawn into the sheath. Thereafter, the sheath is permitted to collapse about the body tissue to contain and constrict the body tissue. Once the body tissue to be resectioned is disposed in the sheath, the sheath is severed to resection the body tissue.

15 Claims, 11 Drawing Sheets

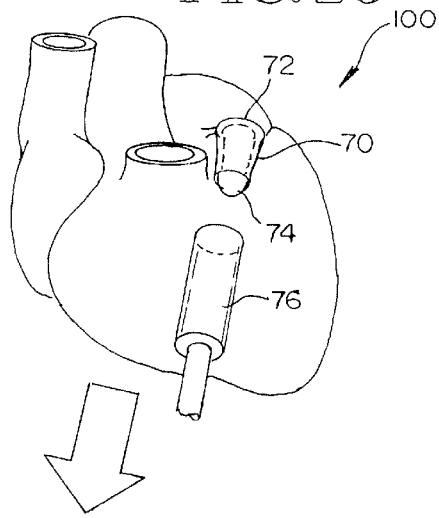
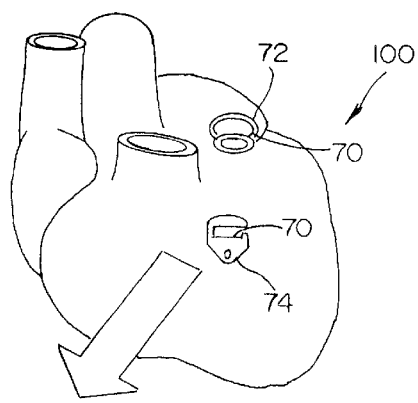
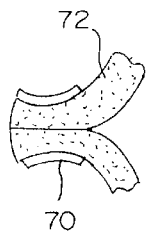
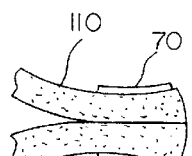
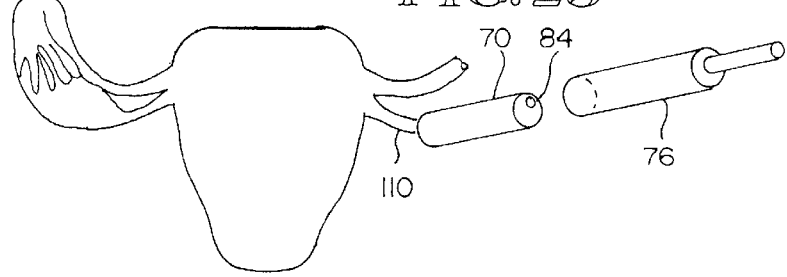
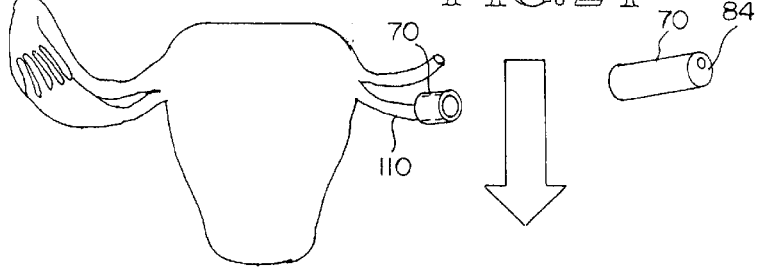

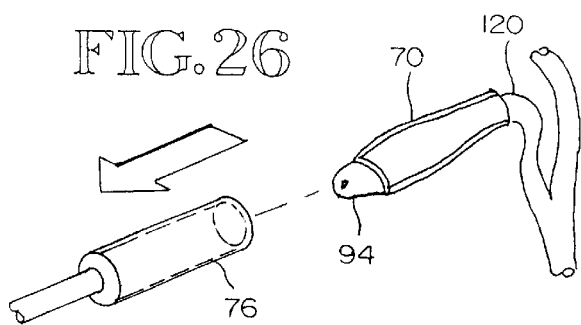
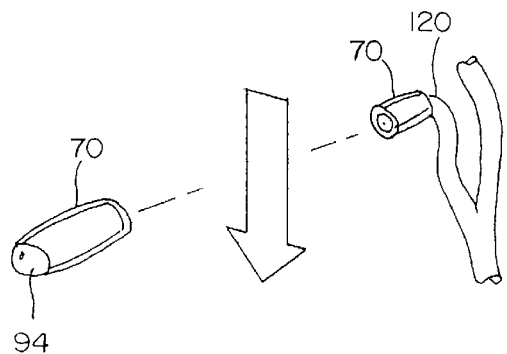
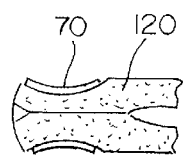
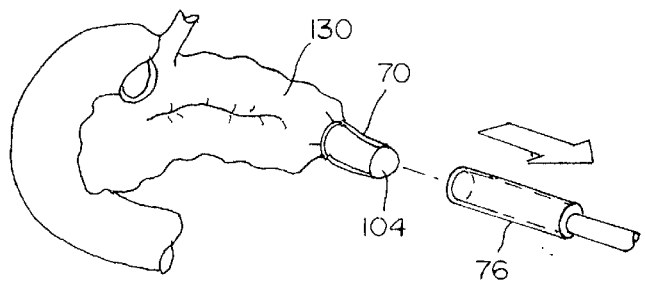
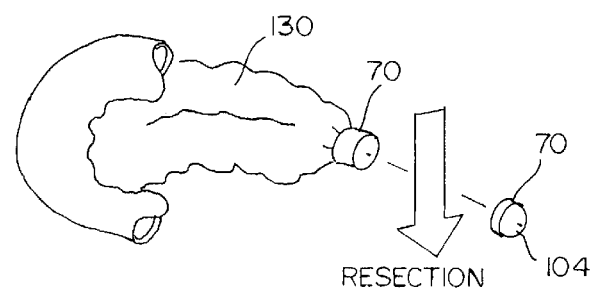
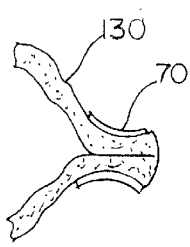

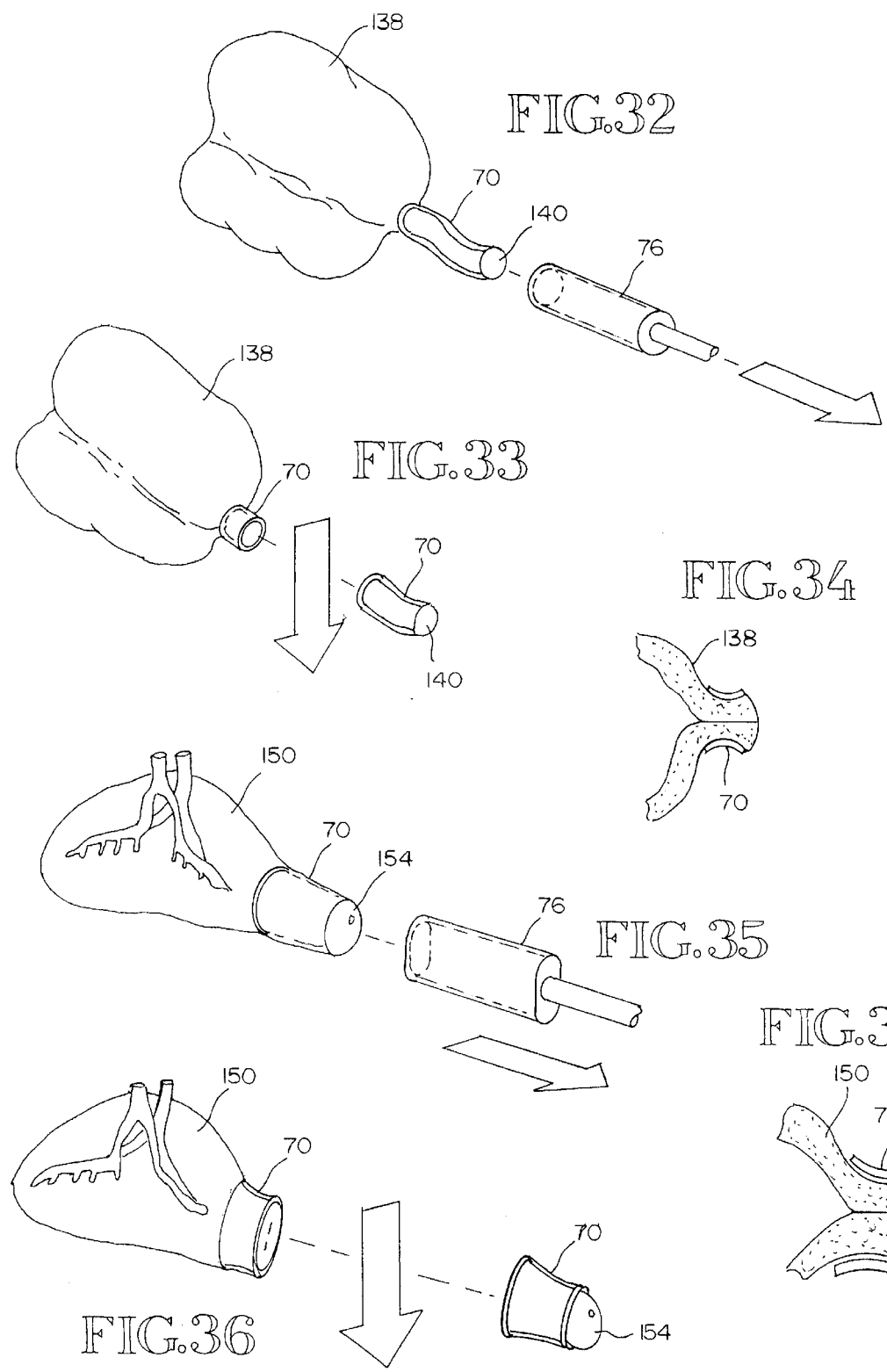

TISSUE RESECTION DEVICE, SYSTEM AND METHOD

RELATED APPLICATION

This application is a continuation of prior application having Ser. No. 09/780,232, filed Feb. 9, 2001, now U.S. Pat. No. 6,485,407, which is a continuation-in-part of prior application having Ser. No. 09/534,244, filed Mar. 23, 2000, now U.S. Pat. No. 6,328,689, the entireties of which are incorporated herein by reference.

BACKGROUND OF THE INVENTION

The present invention is generally directed to an apparatus and method for resectioning body tissue. The present invention is more particularly directed to such an apparatus and method which may be used on various types of body tissue and which greatly simplifies resection procedures.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

About 40 years ago, it was first postulated that the tethering force that tends to keep the intrathoracic airways open was lost in emphysema and that by surgically removing the most affected parts of the lungs, through lung volume reduction surgery (LVRS), the force could be partially restored. Although the surgery was deemed promising, the procedure was abandoned.

Lung volume reduction surgery was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

The improvements in pulmonary function resulting from LVRS cannot be ignored. However, the surgery is very invasive and fraught with complications. Among the complications is the potential for lung air leaks. Lung tissue is very thin, and fragile hence difficult to suture together. After a lung portion is sectioned and removed, the remaining lung is most often restructured with suture staples. In about thirty percent (30%) of the cases, the difficulty with suturing lung tissue results in air leaks. Treatment for such air leaks depends upon their severity and often, in the most serious cases, requires further open chest surgery.

Air leaks in lungs can be caused by other causes. With increasing age, a patient may develop a weakened section of lung which may then rupture due to an extreme pressure differential, such as may result from simply a hard sneeze. Patients with AIDS and pulmonary complications can suffer from air leaks. Air leaks in lungs can further be produced by direct trauma such as a puncture from a broken rib or a stab wound.

The invention disclosed and claimed in copending U.S. Pat. No. 6,328,689 B1 provides an improved therapy for treating COPD. The improved therapy includes a lung constriction device and method for suppressing such air leaks in lung tissue which does not require any suturing of the effected lung tissue. Still further, by constricting a large enough portion of a lung, lung volume reduction with the concomitant improved pulmonary function may be obtained without the need for any suturing of lung tissue at all.

More specifically, the lung constriction device includes a jacket of flexible material configured to cover at least a portion of a lung. The jacket has a pair of opened ends to permit the lung portion to be drawn into the jacket. The jacket is dimensioned to constrict the lung portion after the lung portion is drawn therein. The lung constriction device is preferably formed of expandable material for receiving the lung portion when forced into an expanded enlarged condition by an expansion force, and then contractible about the lung portion upon release of the expansion force for constricting the lung portion.

An important aspect of the device and method disclosed in U.S. Pat. No. 6,328,689 B1 is the ability to sever the constricting device intermediate its ends. This allows a significant portion of the constricted lung tissue to be removed altogether while permitting a portion of the constricting device to remain in the body for continued suppression of air leaks and maintenance of the remaining lung tissue integrity.

Devices and methods similar to those disclosed in U.S. Pat. No. 6,328,689 B1 may be employed to advantage in other and different procedures such as in general resection procedures and for body tissue. Resection procedures are commonly performed for such body tissue as, for example, atrial appendage tissue, ovarian tissue, gall bladder tissue, pancreatic tissue, appendix tissue and spleen tissue. Resection procedures may be required to treat cancer, organ damage, or organ disease, for example.

Common to all resection procedures is the need to isolate the body tissue to be removed, resection the body tissue to be removed, and then suture the incision. All the while, great care must be taken to avoid infection from external sources and from the diseased tissue being removed. Frequent aspiration of blood and other body fluids, some of which may be contaminated, is often essential. The present invention provides an improved method for use in body tissue resection.

SUMMARY OF THE INVENTION

The invention therefore provides a method of resectioning body tissue which may find many applications for encapsulation, isolation, and resection of body tissue. More particularly, among its many applications, the present invention may be employed for removal of diseased tissue, nodules and tumors, for example. The method includes the steps of providing a sheath formed of severable material having opposed opened ends, drawing the body tissue to be resectioned into the sheath to confine and constrict the soft tissue within the sheath, and severing the sheath and the body tissue within the sheath intermediate the opposed opened ends of the sheath.

The invention further provides a device for use in resectioning body tissue. The device comprises a sheath of severable material, the sheath having a pair of opened ends for receiving the body tissue and the sheath being dimensioned for containing and constricting the body tissue.

The invention further provides a system for resectioning body tissue. The system includes a sheath of severable material, the sheath having a pair of opened ends for receiving the tissue and the sheath being dimensioned for containing and constricting the tissue, means for drawing the tissue into the sheath to constrict and isolate the tissue, and means for severing the sheath to resection the tissue.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 20 is a partial perspective view of a heart illustrating a resection device of the present invention constricting a portion of the left atrial tissue after being deployed thereon;

FIG. 21 is a partial perspective view of the heart illustrating the restriction device after being severed for resectioning the left atrial tissue;

FIG. 22 is a partial cross sectional view of the remaining resection device and left atrial tissue after the resection of the left atrium;

FIG. 23 is a perspective view of an ovary illustrating a resection device of the present invention constricting a portion of the ovary tissue after being deployed thereon;

FIG. 24 is a partial perspective view of the ovary illustrating the restriction device after being severed for resectioning the ovary tissue;

FIG. 25 is a partial cross sectional view of the remaining resection device and ovary tissue after the resection of the ovary;

FIG. 26 is a perspective view of a gall bladder illustrating a resection device of the present invention constricting a portion of the gall bladder tissue after being deployed thereon;

FIG. 27 is a partial perspective view of the gall bladder illustrating the restriction device after being severed for resectioning the gall bladder tissue;

FIG. 28 is a partial cross sectional view of the remaining resection device and gall bladder tissue after the resection of the gall bladder;

FIG. 29 is a perspective view of a pancreas illustrating a resection device of the present invention constricting a portion of the pancreas tissue after being deployed thereon;

FIG. 30 is a partial perspective view of the pancreas illustrating the restriction device after being severed for resectioning the pancreas tissue;

FIG. 31 is a partial cross sectional view of the remaining resection device and pancreas tissue after the resection of the pancreas;

FIG. 32 is a partial perspective view of an intestine and appendix illustrating a resection device of the present invention constricting a portion of the appendix tissue after being deployed thereon;

FIG. 33 is a partial perspective view of the intestine and appendix illustrating the restriction device after being severed for resectioning the appendix tissue;

FIG. 34 is a partial cross sectional view of the remaining resection device and intestine and appendix tissue after the resection of the appendix tissue;

FIG. 35 is a perspective view of a spleen illustrating a resection device of the present invention constricting a portion of the spleen tissue after being deployed thereon;

FIG. 36 is a partial perspective view of the spleen illustrating the restriction device after being severed for resectioning the spleen tissue; and FIG. 37 is a partial cross sectional view of the remaining resection device and spleen tissue after the resection of the spleen.

DETAILED DESCRIPTION

Figure 1:
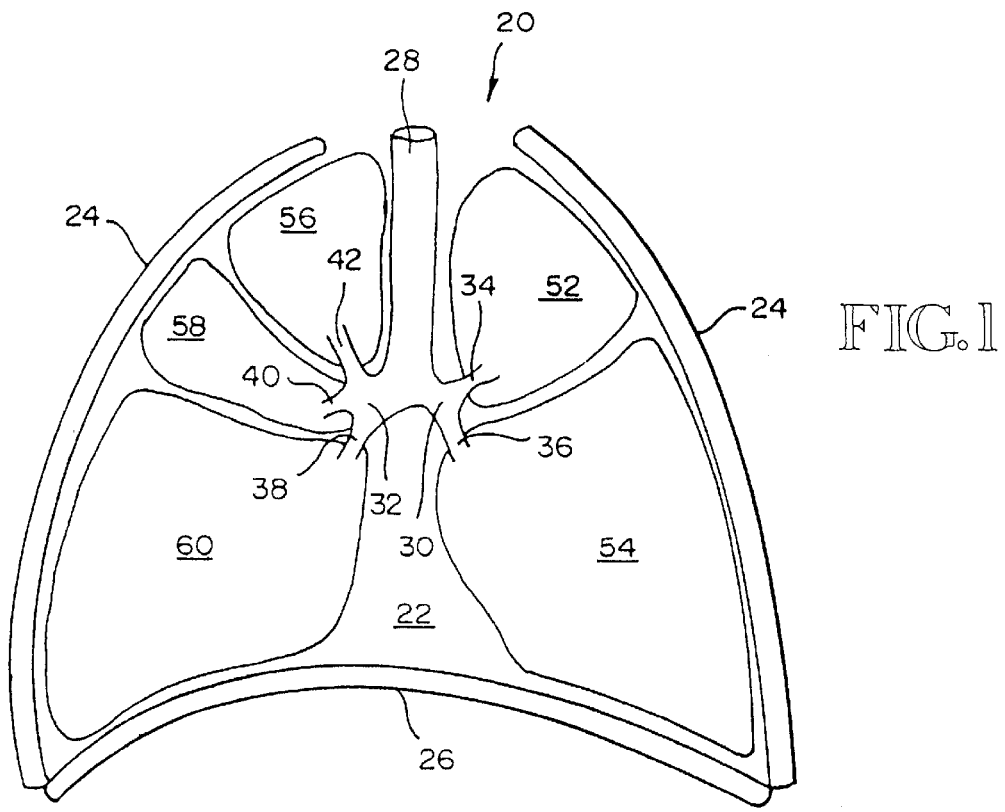
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstem bronchus 30, the right mainstem bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

A healthy respiratory system has an arched or inwardly arcuate diaphragm 26. As the individual inhales, the diaphragm 26 straightens as illustrated in FIG. 1 to increase the volume of the thorax 22. This causes a negative pressure within the thorax. The negative pressure within the thorax in turn causes the lung lobes to fill with air to an inflated condition as illustrated in FIG. 1. When the individual exhales, the diaphragm returns to its original arched condition to decrease the volume of the thorax. The decreased volume of the thorax causes a positive pressure within the thorax which in turn causes exhalation of the lung lobes.

Figure 2:
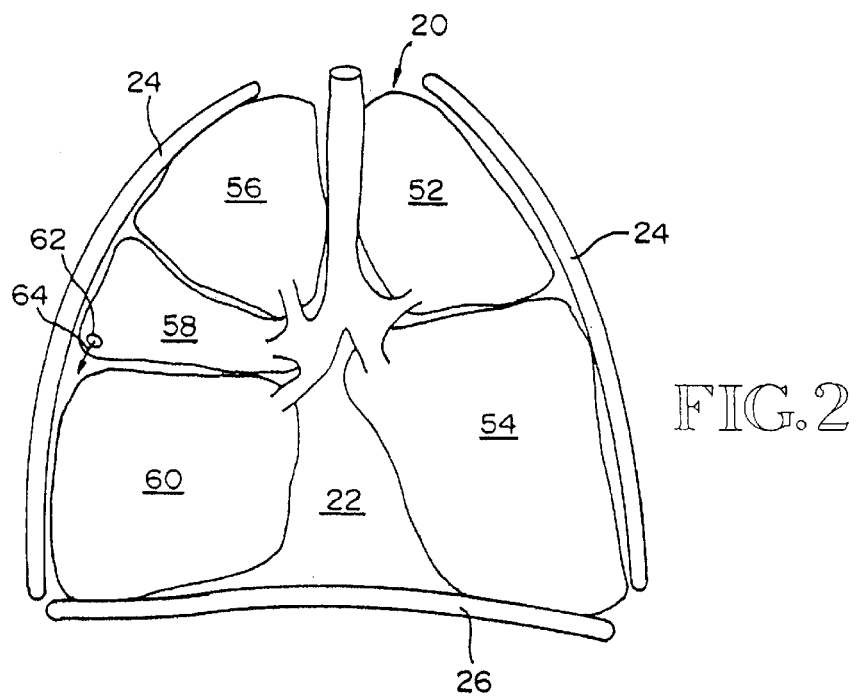
FIG. 2 is a sectional view similar to FIG. 1 but illustrating a respiratory system suffering from an air leak in a lung lobe.
Figure 3:
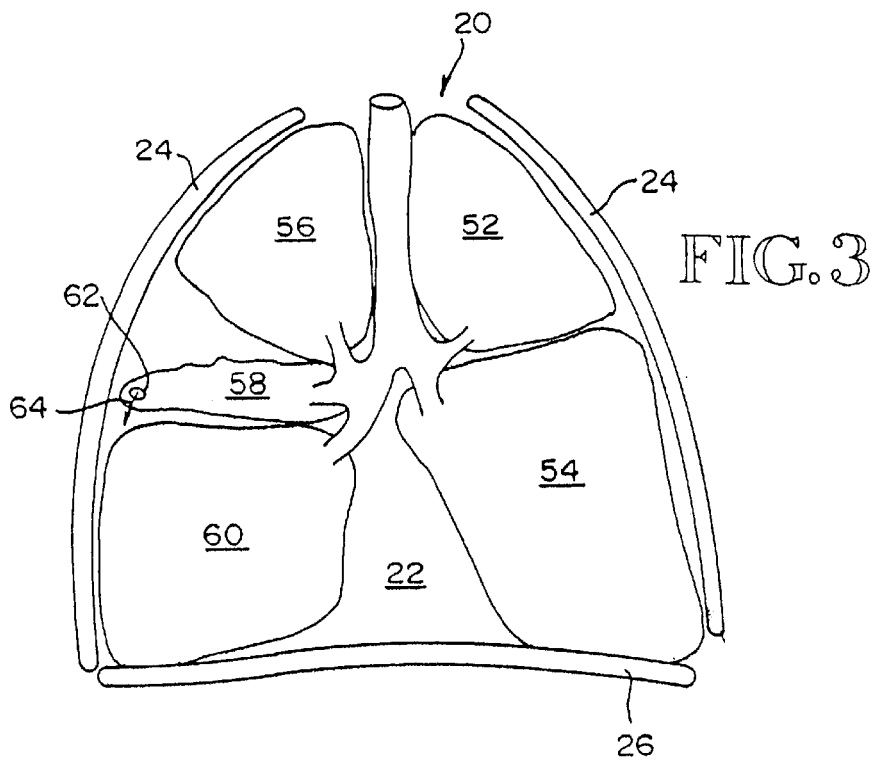
FIG. 3 is a sectional view illustrating the lung lobe having the air leak in a deflated condition due to the air leak.

FIG. 2 illustrates the respiratory system 20 just after suffering an air leak or rupture. Here it may be seen that the rupture 62 has occurred in lung lobe 58. As a result, air is escaping from the lung lobe 58 as indicated by the arrow 64. Hence, this individual is incapable of breathing normally. The negative pressure created by the moving diaphragm 26 causes some of the air taken into lobe 58 to be lost through the rupture 62. When the diaphragm 26 returns to its arched configuration, the positive pressure produced thereby forces still more air from lobe 58 through the rupture. Eventually, within a short time, the lobe 58 collapses as illustrated in FIG. 3 and becomes nonfunctional to support respiration.

Figure 4:
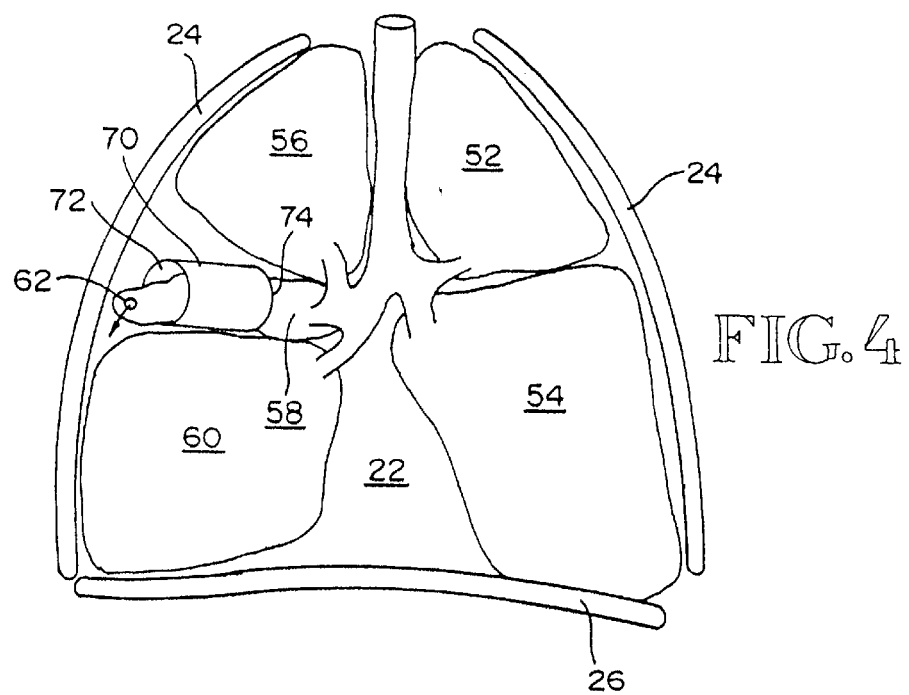
FIG. 4 is a sectional view of the respiratory system of FIG. 2 with a resection device embodying the present invention being disposed over a lung portion to be constricted for suppressing the air leak.

FIG. 4 shows a constriction and resection device 70 embodying the present invention in the process of being deployed on the effected lung lobe 58. The device 70 is configured as a jacket of sheath formed of a sheet or flexible fabric of biocompatible material. The material may be both flexible and expandable material formed from silicone rubber, polyurethane, expanded polytetraflouroethylene, polyester and polyurethane, or nylon and polyurethane, for example. It may alternatively be flexible but nonexpandable formed from nylon, polytetraflouroethylene, or polyester, for example. If the sheath is expandable, it may more specifically be formed from a sheet or fabric of 70% nylon and 30% polyurethane. The sheath is preferably opened at both ends 72 and 74 and, as illustrated, may be generally cylindrical in configuration.

Figure 5:
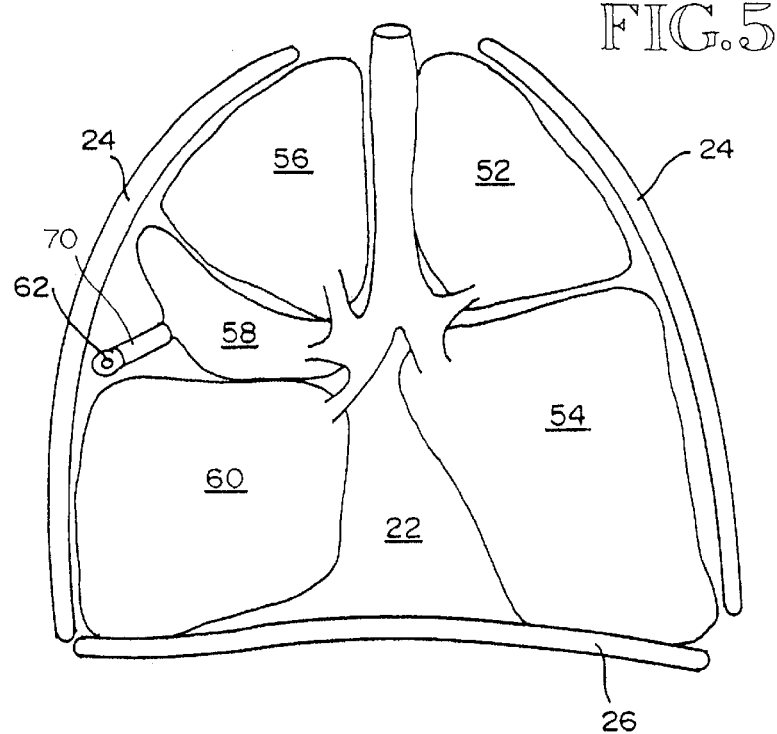
FIG. 5 is a sectional view illustrating the resection device constricting the effected lung portion and suppressing the air leak.

In accordance with one embodiment of the present invention, the sheath is applied to the portion of the lung lobe having the leak or puncture while the jacket is in an expanded condition. This may be accomplished, as will be seen hereinafter, by expanding the jacket and then pulling the lung portion into the jacket. When the effected lung portion is thus disposed with respect to the sheath as illustrated in FIG. 4, the expansion of the device is released as seen, for example, in FIG. 5. With the expansion released, the sheath is permitted to contract or collapse about the lung portion to constrict the lung portion and effectively suppress the leak or puncture.

In accordance with a further embodiment, if the flexible sheath is nonexpandable, the lung tissue may be collapsed as it is pulled into the jacket. Once disposed in the sheath, the lung tissue will remain constricted by the sheath.

When the lung portion is thus constricted, the air leakage will be suppressed. The lung lobe 58 thereafter, during successive breaths, will reinflate and become functional once again to support respiration.

The use of the device 70 need not be restricted to the suppression of air leakages in lungs. It may, for example, find use to advantage in constricting a lung portion suffering from COPD to simulate or achieve lung volume reduction. All of the beneficial effects of lung volume reduction surgery may be realized and, most importantly, without requiring suturing of lung tissue.

Figure 6:
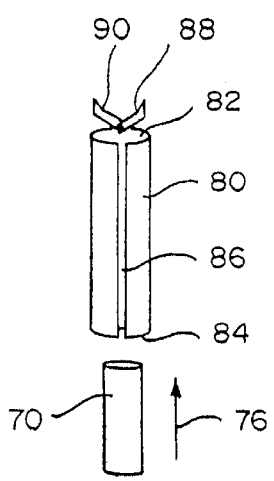
FIG. 6 illustrates a resection device embodying the present invention and a mandrel which may be used in a mechanical method embodying the present invention for deploying the resection device.

FIGS. 6–11 illustrate a mechanical process for deploying the device 70. In an initial step, as illustrated in FIG. 6, the device 70 is first aligned with an expansion mandrel or form 80. The device 70 is then moved towards the form 80 as indicated by the arrow 76.

In accordance with this embodiment, the form 80 is hollow, has opened ends 82 and 84 and has a configuration similar to that of the device 70. In addition, the form has a longitudinal slit 86 rendering the form expandable in a transverse direction. The form further includes tabs 88 and 90 which, when pressed towards each other, cause the form to expand in the transverse direction.

Figure 7:
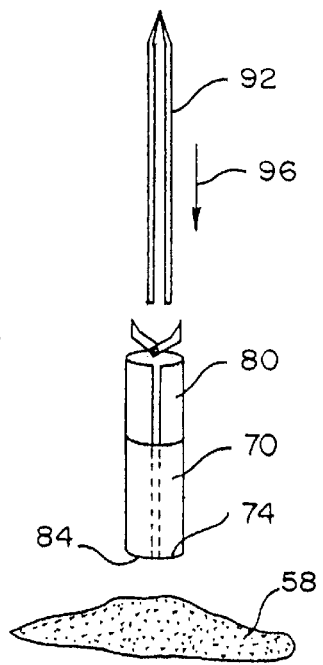
FIG. 7 illustrates an initial step in practicing the mechanical method of deployment embodying the present invention.
Figure 8:
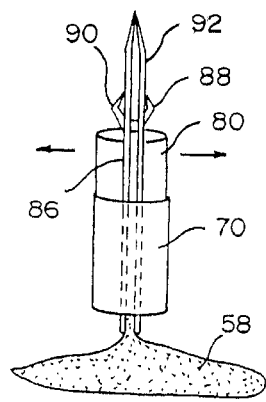
FIG. 8 illustrates a further step in the mechanical deployment of the resection device.

The device 70 is applied to the form 80 until the end 74 of the device 70 is at the end 84 of the form 80 as illustrated in FIG. 7. An atraumatic instrument, such as a forceps 92, is then aligned with the form 80 and moved relative thereto through the form in the direction of arrow 96 and into engagement with the lung tissue 58 as illustrated in FIG. 8.

Figure 9:
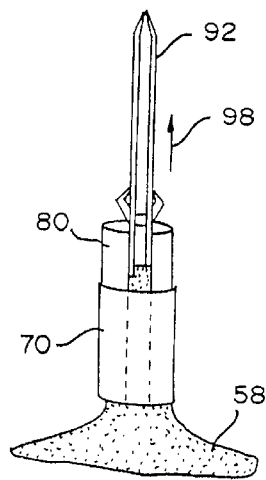
FIG. 9 illustrates the step of pulling the lung portion to be constricted into the resection device in accordance with the mechanical method embodiment.

The forceps 92 are then used to grab the lung tissue 58. Then, the tabs 88 and 90 of the form 80 are pressed toward each other to cause the form 80 to expand in a transverse direction. This may be noticed by the longitudinal slit 86 becoming noticeably wider. The expansion of the form 80 in the transverse direction imparts an expansion force on the device 70, causing it to similarly expand to an expanded condition. With the device 70 thus expanded, the forceps are then retracted as illustrated in FIG. 9 in the direction of arrow 98, to pull the lung tissue into the form 80 and device 70. Preferably, although not necessarily, the lung tissue is pulled until it extends entirely through the device 70.

Figure 10:
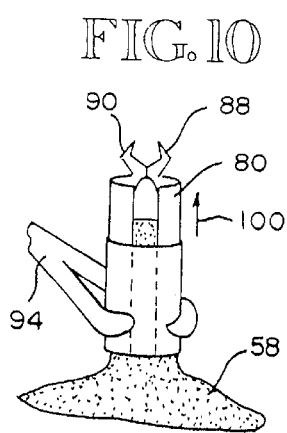
FIG. 10 illustrates the manner in which an expansion force may be released from the resection device as a final step in deploying the resection device in accordance with the mechanical method embodiment.

The process continues as illustrated in FIG. 10. Here, the tabs 88 and 90 are released. Given the volume of lung tissue within the form 80 and device 70, the device 70 remains in an expanded condition. Now, a suitable instrument 94 is used to hold the device 70 in place while the form 80 is moved in the direction of the arrow 100 to withdraw the form 80 from the device 70.

Figure 11:
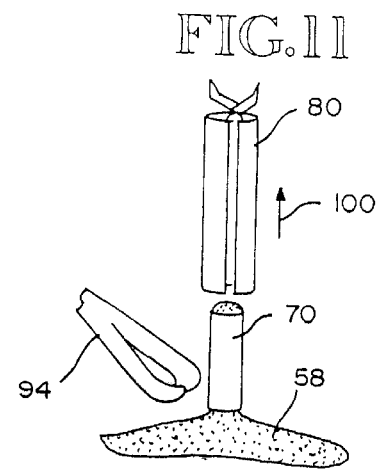
FIG. 11 illustrates the resection device fully deployed as a result of the mechanical method embodiment illustrated in FIGS. 6-10.

As illustrated in FIG. 11, the process is completed when the form 80 is totally withdrawn from the device 70. In doing so, the expansion force applied to the device 70 by the form 80 is released, permitting the device 70 to collapse or contract about the lung tissue 58 drawn into the device 70. The device 70 now constricts the lung tissue to effect air leak suppression or lung volume reduction, for example.

Alternatively, the form 80 need not be expandable if the device 70 is not expandable. Here, the process of pulling the lung tissue into the mandrel 80 and device 70 will cause the lung tissue to collapse. With the device 70 being dimensioned for constricting the lung tissue, once the mandrel is removed, the lung tissue will remain in and be constricted by the device 70 as illustrated in FIG. 11.

The lung tissue within the device 70 is also now ready to be resectioned. This may be accomplished by severing the device 70 intermediate it's ends using an appropriated bladed instrument.

Figure 12:
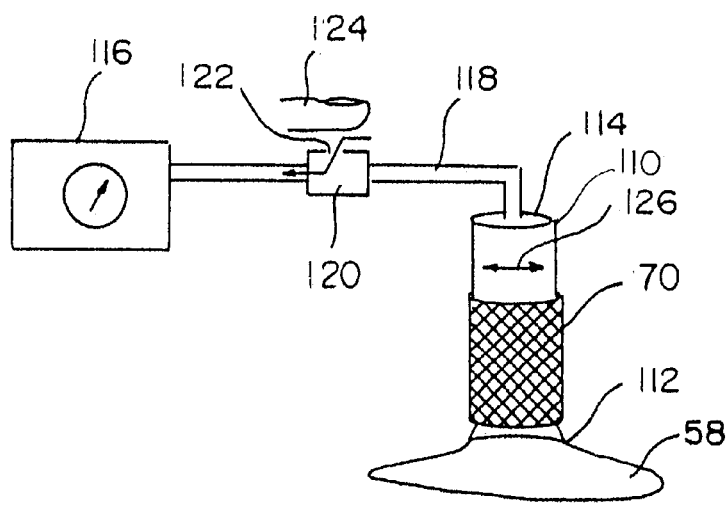
FIG. 12 illustrates an initial step of a further method of deploying the resection device in accordance with further aspects of the present invention.
Figure 13:
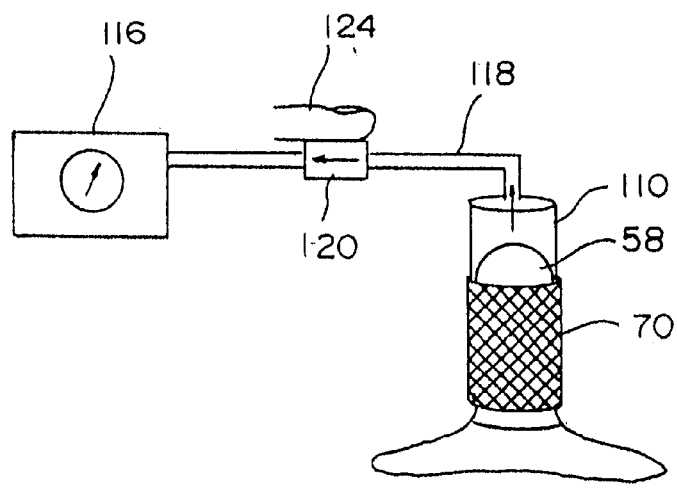
FIG. 13 illustrates an intermediate step in the further method embodiment of deploying the resection device.
Figure 14:
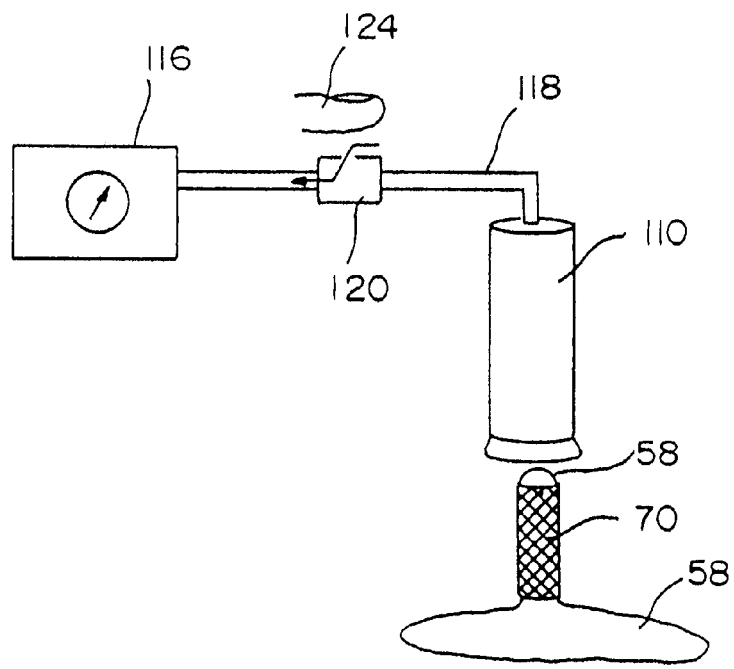
FIG. 14 illustrates a final step in the further method embodiment of deploying the resection device.

FIGS. 12–14 illustrate another embodiment of deploying the device 70 in accordance with further aspects of the present invention. Here, rather than using mechanical pulling of the lung tissue into the device 70, vacuum pressure is utilized instead for pulling the lung tissue into the device 70. This permits the procedure to be more automated and potentially less traumatic to the lung tissue being constricted and resectioned.

As will be noted in FIG. 12, the mandrel or form 110 takes the form of a cylinder having an opened end 112 and a closed end 114. The closed end 114 is coupled to a vacuum source 116 through a conduit 118 and a valve 120. The valve 120 has an aperture 122 which, when closed by, for example, a finger 124, causes the vacuum to be pulled through the conduit 118 and form 110. As illustrated in FIG. 12, the valve is in an opened condition.

The form 110 has a diameter dimension 126 which is substantially greater than the diameter dimension of the device 70 when the device is expandable and in a nonexpanded condition. As seen in FIG. 12, the device 70 has been applied over the form 110 so that the form imparts an expansion force to the device 70. The opened end 112 of the form 110 is in contact with the lung tissue 58 to be constricted and resectioned.

Referring now to FIG. 13, the finger 124 has now closed the valve 120. The vacuum is now being pulled through the conduit 118 and form 110. This causes the lung tissue 58 to be pulled into the form 110 and the device 70 while the device 70 is in an expanded condition.

After the lung tissue 58 has been pulled into the form 110 and the device 70, the device may be held in position and the form 110 withdrawn from the device 70 and the lung tissue 58. When this is completed, as best seen in FIG. 14, the vacuum suction may be released by opening the valve 120. More importantly, the expansion force of the form 110 on the device 70 is released to permit the device 70 to collapse or contract about the lung tissue 58. The device 70 is now deployed for constricting the lung tissue and providing leak suppression or lung volume reduction, for example.

Again, the device 70 need not be expandable. To that end, the form 110 may have the same or approximately the same dimensions as the device 70. When the vacuum suction pulls the lung tissue 58 into the mandrel or form 110, it will collapse. After the vacuum suction is terminated and the mandrel 110 removed, the lung tissue 58 will remain in the device 70 in a collapsed condition to be constricted by the device 70. The lung tissue within the device 70 is also ready to be resectioned. Again, this may be accomplished by severing the device 70 intermediate its ends by use of an appropriate bladed instrument.

Figure 15:
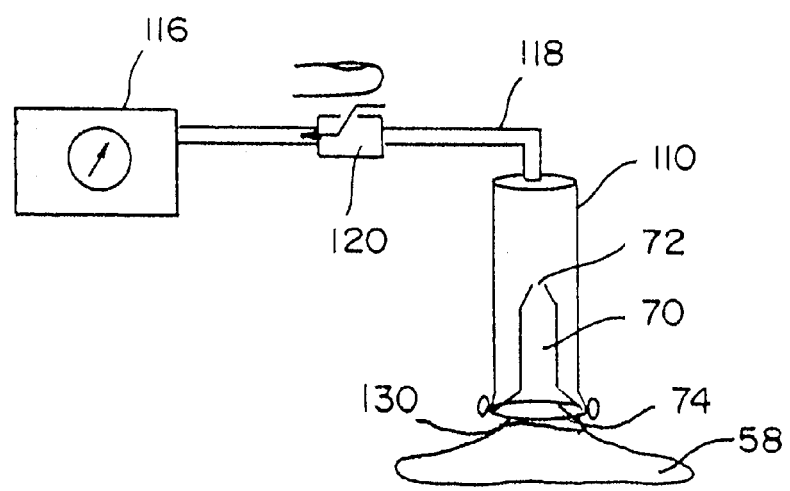
FIG. 15 illustrates an initial step of a still further method of deploying the resection device in accordance with further aspects of the present invention.
Figure 16:
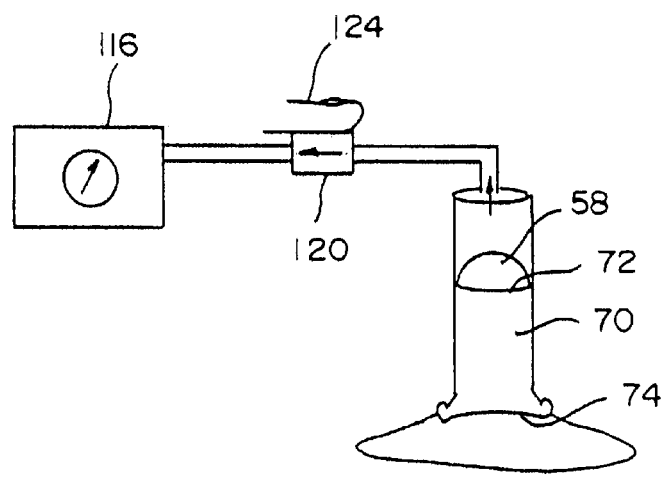
FIG. 16 illustrates an intermediate step in the still further method embodiment of deploying the resection device.
Figure 17:
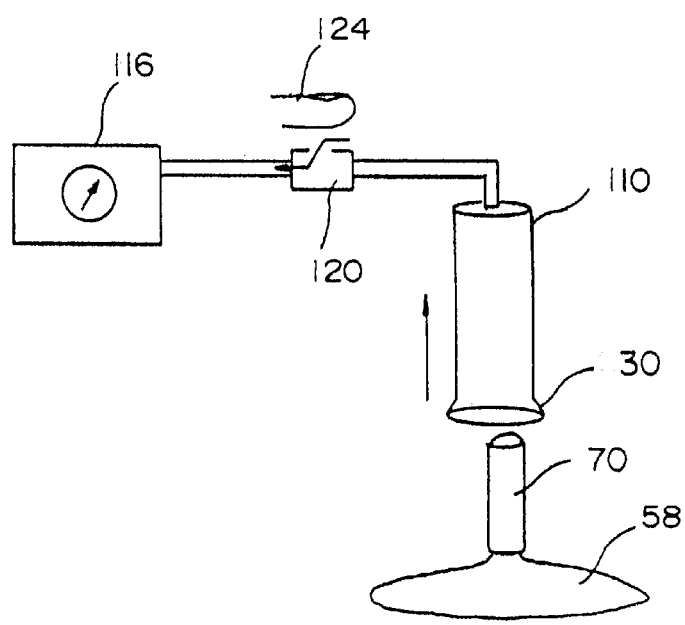
FIG. 17 illustrates a final step in the still further method embodiment of deploying the resection device.

FIGS. 15–17 illustrate a further embodiment of deploying the device 70 on lung tissue 58 to be constricted and resectioned. Here again, a vacuum suction is utilized for pulling the lung tissue into the device 70.

As illustrated in FIG. 15, the vacuum source 116, the conduit 118, and the valve 120 are again used to establish the vacuum suction in the form 110. Here, however, the device 70 is positioned inside of the form 110 with the end 74 of the device 70 being stretched and held by the lip 130 of the form 110. As a result, when the valve 120 is closed, the vacuum is pulled through the mandrel 110 and the device 70 due to the opened end 72 of the device 70.

Now, when the lung tissue 58 is brought into engagement with the end 74 of the device 70 and the vacuum is pulled with the closure of valve 120, the lung tissue is pulled directly into the device 70 as illustrated in FIG. 16. The vacuum is pulled until the lung tissue 58 to be constricted preferably extends entirely through the device 70 past the end 72. As will be further noted, the lung tissue itself exerts an expansion force on the device 70 as the lung tissue is pulled into the device 70.

After the lung tissue 58 has been pulled into the device 70, the end 74 of the device 70 may be released from the lip 130 of the form 110 to permit the form 110 to be withdrawn from the device 70. When this is completed, as best seen in FIG. 17, the vacuum suction may be released by opening the valve 120. The release of the vacuum also releases the expansion force on the device 70. With the expansion force released, the device is permitted to collapse or contract about the lung tissue 58. The device 70 is now deployed for constricting the lung tissue and providing leak suppression or lung volume reduction, for example. The lung tissue 58 within the device 70 is also in condition for resection. Again, the tissue 58 may be resectioned by severing the device 70 intermediate its ends with a suitable bladed instrument.

Once again, the device 70 need not be expandable. To that end, the form or mandrel 110 may be of the same dimension or slightly larger dimension than the device 70 to permit an effective seal between the lip 130 of mandrel or form 110 and the end 74 of the device 70. The vacuum suction will still be pulled through the form 110 and the device 70. As the vacuum suction pulls the lung tissue into the device 70, the lung tissue collapses. When the vacuum is released and the form 110 is removed, the collapsed lung tissue will remain constricted in the device 70 to provide, for example, lung leakage suppression or lung volume reduction.

Figure 18:
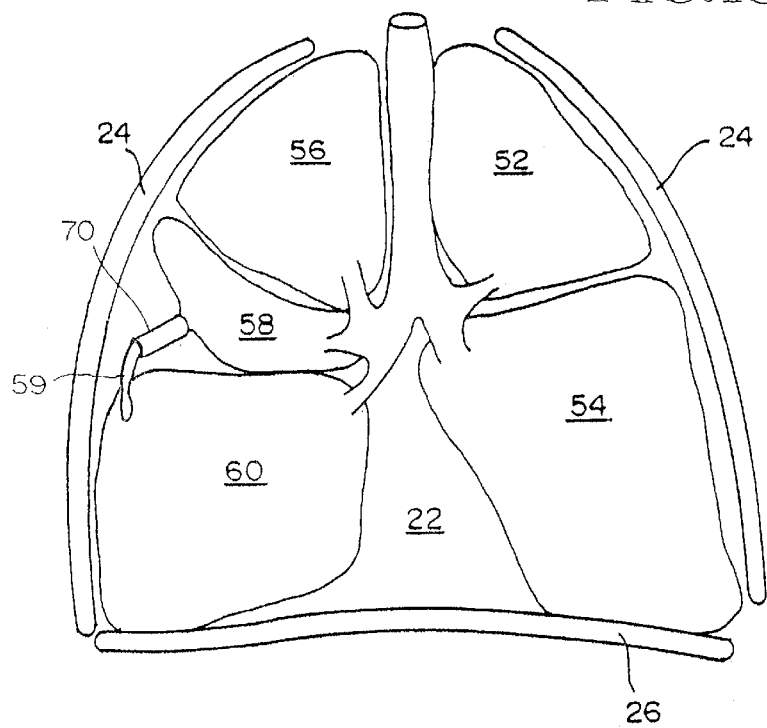
FIG. 18 is a sectional view illustrating the resection device constricting a lung portion to be resectioned for lung volume reduction.
Figure 19:
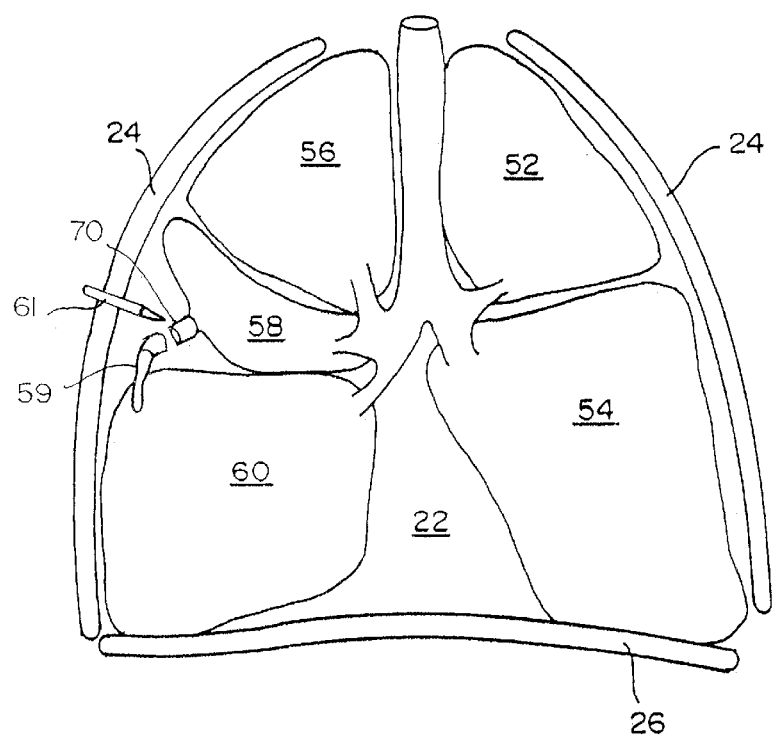
FIG. 19 illustrates the lung portion after being resectioned in accordance with a further embodiment of the present invention.

Referring now to FIGS. 18 and 19, they more clearly illustrate the manner in which the device 70 may be employed for resectioning the lung tissue to effect lung volume reduction to a greater extent. In accordance with this embodiment, the lung portion 59 of lobe 58 has been pulled through the device 70 and is being constricted by the device 70. The device 70 and the manner of pulling the lung portion 59 therethrough may conform to any of the embodiments previously described herein.

In accordance with this embodiment, the device 70 is formed of severable material, such as, any of the materials previously described. This enables the device 70 to be severed or cut intermediate its ends with a suitable bladed instrument 61 as illustrated in FIG. 19 to section the lung portion 59. The portion of the device 70 remaining on the lobe 58 continues to constrict the lung tissue therein to form an effective seal from leakage. Hence, in accordance with this embodiment of the present invention, lung volume reduction is rendered an available treatment while negating the need of conventional lung sectioning and suturing thus avoiding the potentially severe complications which accompany those procedures.

Referring now to FIGS. 20–22, they illustrate the manner in which the device 70 may be utilized for resectioning heart tissue, such as left atrial appendage tissue. Shown in FIG. 20 is a heart 100 having the device 70 deployed on the left atrial appendage 72. The device 70 may be deployed in accordance with any of the previously described methods for deployment. Preferably, the device 70 is deployed by imparting vacuum suction to the left atrial tissue 74 to be resectioned by a vacuum cylinder 76.

Once the device 70 is deployed as illustrated, the tissue 74 constricted within the device 70 and to be resectioned is resectioned as illustrated in FIG. 21. Here it may be seen that the device 70 has been severed intermediate its ends. This results in the resectioning of the tissue 74. The portion of the device 70 remaining on the left atrial appendage, as seen in FIG. 22, continues to constrict the remaining left atrial appendage tissue 72 and maintains the integrity of the left atrial appendage 72 to prevent leakage and bleeding.

As can thus be seen, in accordance with the present invention, resectioning of the heart may be accomplished without suturing by use of the constriction and resection device 70. This will greatly assist in accelerating the healing process and reducing the potential for infection.

Referring now to FIGS. 23–25, they illustrate the manner in which the device 70 may be utilized for resectioning ovarian tissue. Shown in FIG. 23 is an ovary 110 having the device 70 deployed thereon. The device 70 may be deployed in accordance with any of the previously described methods for deployment. Preferably, the device 70 is deployed by imparting vacuum suction to the ovarian tissue 84 to be resectioned by the vacuum cylinder 76.

Once the device 70 is deployed as illustrated, the tissue 84 constricted within the device 70 and to be resectioned is resectioned as illustrated in FIG. 24. Here it may be seen that the device 70 has been severed intermediate its ends. This results in the resectioning of the tissue 84. The portion of the device 70 remaining on the ovary 110, as seen in FIG. 25, continues to constrict the remaining ovarian tissue 110 and maintains the integrity of the ovary 110 to prevent leakage and bleeding.

Referring now to FIGS. 26-29, they illustrate the manner in which the device 70 may be utilized for resectioning gall bladder tissue. Shown in FIG. 26 is a gall bladder 120 having the device 70 deployed thereon. Again, the device 70 may be deployed in accordance with any of the previously described methods for deployment but preferably is deployed by imparting vacuum suction to the gall bladder tissue 94 to be resectioned by the vacuum cylinder 76.

Once the device 70 is deployed as illustrated, the gall bladder tissue 94 constricted within the device 70 and to be resectioned is resectioned as illustrated in FIG. 27. Here it may be once again seen that the device 70 has been severed intermediate its ends. This results in the resectioning of the tissue 94. The portion of the device 70 remaining on the gall bladder 120, as seen in FIG. 28, continues to constrict the gall bladder tissue 120 to maintain its integrity and to prevent leakage and bleeding.

Referring now to FIGS. 29–31, they illustrate the manner in which the device 70 may be utilized for resectioning pancreatic tissue. Shown in FIG. 29 is a pancreas 130 having the device 70 deployed thereon. The device 70 is preferably deployed by imparting vacuum suction to the pancreatic tissue 104 to be resectioned by the vacuum cylinder 76. Of course, any of the other methods of deployment may be used as well.

Once the device 70 is deployed as illustrated, the tissue 104 constricted within the device 70 and to be resectioned is resectioned as illustrated in FIG. 30. Here it may be seen that the device 70 has been severed intermediate its ends. This results in the resectioning of the tissue 104. The portion of the device 70 remaining on the pancreas 130, as seen in FIG. 31, continues to constrict the remaining pancreatic tissue 130 and maintains the integrity of the pancreas to prevent leakage and bleeding.

FIGS. 32–34 illustrate the manner in which the device 70 may be utilized for resectioning an appendix 140 from its adjoining intestine 138. Shown in FIG. 32 is device 70 deployed over the appendix 140. Again, the device 70 may be deployed in accordance with any of the previously described methods for deployment. Preferably, the device 70 is deployed by imparting vacuum suction to the appendix tissue 140 to be resectioned by the vacuum cylinder 76.

Once the device 70 is deployed on the appendix as illustrated, the appendix tissue 140 constricted within the device 70 and to be resectioned is resectioned as illustrated in FIG. 33. Here it may be seen that the device 70 has been severed intermediate its ends. This results in the resectioning of the appendix 140. The portion of the device 70 remaining on what remains of the appendix 140, as seen in FIG. 34, maintains the integrity of the intestine 138 to prevent leakage and bleeding.

Referring now to FIGS. 35–37, they illustrate a last example as to how the device 70 may be utilized for resectioning body tissue. Here, spleen tissue is to be resectioned. Shown in FIG. 35 is a spleen 150 having the device 70 deployed thereon. As previously described, the device 70 may be deployed in accordance with any of the previously mentioned methods for deployment. Again, preferably, the device 70 is deployed by imparting vacuum suction to the spleen tissue 154 to be resectioned by a vacuum cylinder 76.

Once the device 70 is deployed as illustrated, the tissue 154 constricted within the device 70 and to be resectioned is resectioned as illustrated in FIG. 36. Again, the device 70 has been severed intermediate its ends. This results in the resectioning of the tissue 154. The portion of the device 70 remaining on the spleen 150, as seen in FIG. 22, continues to maintain the integrity of the spleen 150 to prevent leakage and bleeding.

As can thus be seen, in accordance with the present invention, the resectioning may be accomplished without suturing by use of the constricting and resection device 70. This significantly simplifies resectioning procedures. For example, since a vacuum may be utilized to pull the tissue to be resectioned into the device, the area is also aspirated at the same time. This assists in preventing contamination and infection. Also, there is no resulting opened wound by virtue of the resection. This again lends to assist in preventing infection. Resection is rendered substantially an automated procedure since the procedures for deploying the device may be automated. Hence, the present invention provides an improved device and method which may be used to advantage for resectioning body tissue.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable device for constricting and collapsing a body organ, the device comprising an elongated sleeve having opposed ends with one end being open for receiving the body organ within the sleeve, the sleeve being formed from a material expandable to receive therein the body organ to be constricted when in an expanded condition and to constrict and collapse therein the bode organ when released from the expanded condition.

2. The device of claim 1, wherein the sheath is severable intermediate to the ends while in the body.

3. The device of claim 1, wherein the elongated sleeve is arranged to constrict the body organ to an extent necessary to limit air leakage from the body organ when released from the expanded condition.

4. The device of claim 1, wherein the elongated sleeve is arranged to constrict the body organ an extent necessary to limit blood circulation in the body organ when released from the expanded condition.

5. The device of claim 1, wherein the elongated sleeve is arranged to constrict the body organ to an extent necessary to promote infarction and fibrosis in the body organ when released from the expanded condition.

6. The device of claim 1, wherein another end is open.

7. The device of claim 1, wherein the another end is open for access to the portion of the sleeve arranged for receiving therein the body organ to be constricted.

8. An implantable device for constricting a body organ, the device comprising an elongated sleeve arranged to receive therein the body organ to be constricted and having a pair of opposed open ends for receiving the body organ within the sleeve, the sleeve being dimensioned for constricting the body organ within to an extent to suppress leakage of at least one of body fluid and air.

9. The device of claim 8, wherein the sleeve is severable intermediate to the ends while in the body.

10. A device for resectioning body organ, comprising a sheath means for constricting the body tissue to an extent necessary to suppress leakage of at least one of body fluid and air, the sheath means being configured to sheathe the body organ and be severable into at least one body organ constricting portion.

11. An implantable device for constricting a body organ, the device comprising an elongated sleeve having opposed ends with one end being open for receiving the body organ within the sleeve, the sleeve being formed from a material expandable to receive therein the body organ to be constricted when in an expanded condition and to constrict therein the body organ when released from the expanded condition an extent necessary to limit blood circulation in the body organ when released from the expanded condition.

12. The device of claim 11, wherein the elongated sleeve is arranged to constrict the body organ to an extent necessary to promote infarction and fibrosis in the body organ when released from the expanded condition.

13. The device of claim 11, wherein the elongated sleeve is severable intermediate to its ends.

14. The device of claim 11, wherein the sleeve has a second end being open for allowing the organ to extend through the sleeve.

15. the device of claim 11, further comprising a retaining structure for inhibiting the removal of the sleeve from the organ.

* * * * *

UNITED STATES PATENT AND TRADEMARK OFFICE
CERTIFICATE OF CORRECTION

PATENT NO. : 6,790,172 B2  
DATED : September 14, 2004  
INVENTOR(S) : Clifton A. Alferness and Hugo X. Gonzalez Page 1 of 1

It is certified that error appears in the above-identified patent and that said Letters Patent is hereby corrected as shown below:

Column 10,  
Line 52, delete "bode" and insert -- body --, therefor.  
Line 61, after "organ" insert -- to --, therefor.

Column 12,  
Line 17, delete "the" and insert -- The --, therefor.

Signed and Sealed this

Thirteenth Day of December, 2005

JON W. DUDAS  
*Director of the United States Patent and Trademark Office*